(12) United States Patent
Krumm et al.

(10) Patent No.: US 11,242,305 B2
(45) Date of Patent: Feb. 8, 2022

(54) REACTIVE DISTILLATION FOR FORMING SURFACTANTS

(71) Applicant: SIRONIX RENEWABLES, INC., Seattle, WA (US)

(72) Inventors: Christoph Krumm, Seattle, WA (US); Connor Beach, Seattle, WA (US); Shawn Eady, Seattle, WA (US)

(73) Assignee: Sironix Renewables, Inc., Seattle, WA (US)

( * ) Notice: Subject to any disclaimer, the term of this patent is extended or adjusted under 35 U.S.C. 154(b) by 15 days.

(21) Appl. No.: 16/771,250

(22) PCT Filed: Dec. 14, 2018

(86) PCT No.: PCT/US2018/065723
§ 371 (c)(1),
(2) Date: Jun. 10, 2020

(87) PCT Pub. No.: WO2019/118862
PCT Pub. Date: Jun. 20, 2019

(65) Prior Publication Data
US 2021/0087124 A1    Mar. 25, 2021

Related U.S. Application Data

(60) Provisional application No. 62/599,092, filed on Dec. 15, 2017.

(51) Int. Cl.
| | |
|---|---|
| C07C 27/00 | (2006.01) |
| C07D 307/00 | (2006.01) |
| B01D 3/00 | (2006.01) |
| C07C 27/22 | (2006.01) |
| B01D 3/14 | (2006.01) |
| B01D 3/32 | (2006.01) |
| C07C 49/21 | (2006.01) |
| C07D 307/36 | (2006.01) |

(52) U.S. Cl.
CPC ............ *C07C 27/22* (2013.01); *B01D 3/009* (2013.01); *B01D 3/146* (2013.01); *B01D 3/32* (2013.01); *C07C 49/21* (2013.01); *C07D 307/36* (2013.01)

(58) Field of Classification Search
CPC ........ C07C 27/22; C07D 307/36; B01D 3/009
See application file for complete search history.

(56) References Cited

U.S. PATENT DOCUMENTS

| | | |
|---|---|---|
| 2,411,567 A | 11/1946 | Wotherspoon |
| 4,443,559 A | 4/1984 | Smith, Jr. |
| 4,477,382 A | 10/1984 | Goel et al. |
| 5,338,517 A | 8/1994 | Evans, III et al. |
| 5,387,705 A | 2/1995 | Stipp et al. |
| 5,776,320 A | 7/1998 | Marion et al. |
| 6,149,879 A | 11/2000 | Forestiere et al. |
| 6,416,659 B1 | 7/2002 | Groten et al. |
| 2004/0260137 A1 | 12/2004 | Elomari et al. |
| 2014/0135359 A1 | 5/2014 | Martineau |
| 2015/0150768 A1 | 6/2015 | West et al. |
| 2015/0166596 A1 | 6/2015 | Hill |
| 2016/0304479 A1 | 10/2016 | Stensrud |
| 2017/0226075 A1 | 8/2017 | Stensrud et al. |
| 2018/0051113 A1 | 2/2018 | Yang et al. |

FOREIGN PATENT DOCUMENTS

| | | |
|---|---|---|
| CN | 104162447 B | 11/2017 |
| WO | 1996027580 A1 | 9/1996 |
| WO | 2017079718 A1 | 5/2017 |
| WO | 2017079719 A1 | 5/2017 |
| WO | 2019040389 A1 | 2/2019 |
| WO | 2020227097 A1 | 11/2020 |

OTHER PUBLICATIONS

Engel et al., "Thermoreversible reactions on inorganic nanoparticle surfaces: Diels-Alder reactions on sterically crowded surfaces," Chemistry of Materials, vol. 25, Dec. 12, 2012, pp. 149-157.
Naik et al., "Liquid phase acylation of 2-methylfuran with fatty acid anhydride," NAM 26, 2019 North American Catalysis Society Meeting, Jun. 26, 2019, 3 pages.
Pubchem, Compound Summary for SID 150925859, Modify Date: Jun. 3, 2019 [retrieved on Apr. 13, 2021]. Retrieved from the Internet: <URL: https://pubchem.ncbi.nlm.nih.gov/substance/150925859>, 7 pages.
Vauthier et al., "Interfacial Diels-Alder reaction between furan-functionalized polymer coatings and maleimide-terminated poly(ethylene glycol)," The Journal of Physical Chemistry C, vol. 123, Jan. 22, 2019, pp. 4125-4132.
Ackman et al., "Ozonolysis of Unsaturated Fatty Acids I. Ozonolysis of Oleic Acid," Canadian Journal of Chemistry, vol. 39, No. 10, 1961, pp. 1956-1963.
Almqvist, "Furans from biomass: Production, applications and techno economic potential," Processum, Apr. 20, 2018, 9 pages.
Ben-Daniel et al., "Selective Aerobic Oxidation of Alcohols with a Combination of a Polyoxometalate and Nitroxyl Radical as Catalysts," Journal of Organic Chemistry, vol. 66, No. 25, Nov. 2001, pp. 8650-8653.
Bidange et al., "Ethenolysis: A Green Catalytic Tool to Cleave Carbon-Carbon Double Bonds," Chemistry A European Journal, vol. 22, No. 35, Aug. 22, 2016, pp. 12226-12244.

(Continued)

*Primary Examiner* — Sikarl A Witherspoon
(74) *Attorney, Agent, or Firm* — Fredrikson & Byron, P.A.

(57) ABSTRACT

Devices, systems, and methods for forming furan based surfactants by reactive distillation are disclosed herein. Various embodiments can provide a consolidated reaction process that uses reactive distillation to synthesize oleo-furan surfactant molecules and intermediates by combining reaction and separation steps into a single reaction unit or a number of connected reaction units. The single reaction unit or a number of connected reaction units can include a catalyst bed and act to separate reaction side products at opposing ends of the unit or units.

20 Claims, 2 Drawing Sheets

(56) References Cited

OTHER PUBLICATIONS

Brown et al., "The Condensation of Furan and Sylvan with Some Carbonyl Compounds," Canadian Journal of Chemistry, vol. 34, No. 9, Sep. 1956, pp. 1147-1153.
Corberan et al., "Green oxidation of fatty alcohols: Challenges and opportunities," Applied Catalysis A: General, vol. 474, Mar. 2014, pp. 211-223.
Froidevaux et al, "Study of the Diels-Alder and retro-Diels-Alder reaction between furan derivatives and maleimide for the creation of new materials," RSC Advances, vol. 5, 2015, pp. 37742-37754, Abstract Only.
Gandini, "The furan/maleimide Diels-Alder reaction: A versatile click-unclick tool in macromolecular synthesis," Progress in Polymer Science, vol. 38, No. 1, Jan. 2013, pp. 1-29, Abstract Only.
Gheneim et al., "Diels-Alder reactions with novel polymeric dienes and dienophiles: synthesis of reversibly cross-linked elastomers," Macromolecules, vol. 35, No. 19, Aug. 8, 2002, pp. 7246-7253, Abstract Only.
Hong et al., "Selective oxidation of octadecan-1-ol to octadecanoic acid over Co3O4/SiO2 catalysts," Reaction Kinetics and Catalysis Letters, vol. 81, Jan. 2004, pp. 13-20.
Iovel et al., "Hydroxymethylation of Furan and its Derivatives in the Presence of Cation-Exchange Resins," Journal of Molecular Catalysis, vol. 57, No. 1, 1989, pp. 91-103.
Joseph, "Tunable Synthesis and Characterization of Oleo-Furan Sulfonate Surfactants from Renewable Furan and Fatty Acids," Dissertation submitted to the Faculty of University of Minnesota, May 2018, pp. 1-154.
Kadesch, "Ozonolysis of Fatty Acids and Their Derivatives," Progress in the Chemistry of Fats and other Lipids vol. 6, 1963, pp. 291-312.
Kan et al., "Catalytic oxidation of α-eicosanol into eicosanic acid in the presence of Ti-MCM-41 or active component supported Ti-MCM-41 catalysts," Microporous and Mesoporous Materials, vol. 44-45, Apr. 2001, pp. 609-617.
Liang et al., "Acid-Catalyzed Ring Opening of Furan in Aqueous Solution," Energy Fuels, vol. 32, No. 4, 2018, pp. 4139-4148.
Lundin et al., "Intensified and Safe Ozonolysis of Fatty Acid Methyl Esters in Liquid CO2 in a Continuous Reactor," AIChE Journal, vol. 63, No. 7, 2017, pp. 2819-2826.
Pubchem. CID 54467179, Retrieved from the Internet <https://pubchem.ncbi.nlm.nih.gov/compound/54467179>, Dec. 4, 2011, pp. 1-6.
Pubchem. CID 68119, Retrieved from the Internet <https://pubchem.ncbi.nlm.nih.gov/compound/68119>, Mar. 26, 2005, pp. 1-19.
Saedi et al., "MIL-101 metal-organic framework: A highly efficient heterogeneous catalyst for oxidative cleavage of alkenes with H2O2," Catalysis Communications, vol. 17, Jan. 5, 2012, pp. 18-22.
Saha et al., "Advances in 5-hydroxymethylfurfural production from biomass in biphasic solvents," Green Chemistry, vol. 16, 2014, pp. 24-38.
Shi et al., "Au—Pd nanoparticles on layered double hydroxide: Highly active catalyst for aerobic oxidation of alcohols in aqueous phase," Catalysis Communications, vol. 18, Feb. 2002, pp. 142-146.
Travis et al., "Osmium Tetroxide-Promoted Catalytic Oxidative Cleavage of Olefins: An Organometallic Ozonolysis," Journal of the American Chemical Society, vol. 124, No. 9, 2002, pp. 3824-3825.
International Patent Application No. PCT/US2018/065723, International Search Report and Written Opinion dated Feb. 21, 2019, 9 pages.
Park et al., "Tunable Oleo-Furan Surfactants by Acylation of Renewable Furans," ACS Central Science, vol. 2, No. 11, 2016, pp. 820-824.
Trubyanov et al., "High-pressure distillation: Simultaneous impact of pressure, temperature and loading on separation performance during distillation of high-purity gases in high-performance randomly-packed columns," Separation and Purification Technology, vol. 135, Oct. 2014, pp. 117-126.
Byrne et al., "Tools and techniques for solvent selection: green solvent selection guides," Sustainable Chemical Processes, vol. 4, No. 7, 2016, 24 pages.
Yow et al., "Hydrolysis of palm olein catalyzed by solid heteropolyacids," Journal of the American Oil Chemists' Society, vol. 79, 2002, pp. 357-361.
Liu et al., "Molybdenum Oxide-Modified Iridium Catalysts for Selective Production of Renewable Oils for Jet and Diesel Fuels and Lubricants," ACS Catalysis, vol. 9, Jul. 16, 2019, pp. 7679-7689.
Pubmed Compound Record for CID 14421037, '2-Ethyl-5-hexylfuran-3-sulfonicacid', U.S. National Library of Medicine, Feb. 9, 2007, retrieved from https://pubchem.ncbi.nlm.nih.gov/compound/14421037, 10 pages.
European Patent Application No. 18888320.1, Extended European Search Report dated Jun. 9, 2021, 7 pages.
Sakuth et al., "Reactive Distillation," Ullmann's Encyclopedia of Industrial Chemistry, Jan. 1, 2012, Wiley-VCH, Weinheim, pp. 263-276.
Pubmed Compound Record for CID 75388835, 'Methyl 4-[(3,5-dimethylphenoxy)sulfonyl]-5-methylfuran-2-carboxylate', U.S. National Library of Medicine, Jul. 12, 2014, pp. 1-9 (https://pubchem.ncbi.nlm.nih.gov/compound/75388835).
Xu et al., "Trialkylphosphine-Mediated Synthesis of 2-Acyl Furans from Ynenones," Organic Letters, vol. 19, Jun. 27, 2017, pp. 3556-3559.
Pubmed Compound Record for CID 13090063, '4-Sulfo-5-methylfuran-2-carboxylic acid', U.S. National Library of Medicine, Feb. 8, 2007, pp. 1-10 (https://pubchem.ncbi.nlm.nih.gov/compound/13090063).

REACTIVE DISTILLATION FOR FORMING SURFACTANTS

RELATED APPLICATION

This application is a National Stage filing from International Patent Application No. PCT/US2018/065723, filed Dec. 14, 2018, which claims the benefit of U.S. Provisional Application No. 62/599,092 filed Dec. 15, 2017, the contents of which are hereby incorporated by reference.

TECHNICAL FIELD

This disclosure generally relates to devices, systems, and methods for forming surfactants. In particular, embodiments described herein include devices, systems, and methods for forming furan based surfactants by reactive distillation.

BACKGROUND

Surfactants are chemical compounds that have a variety of applications. Such applications can include household cleaners and detergents, institutional & industrial cleaning products, agricultural chemicals such as spray adjuvants, oilfield applications, and various coating additives. Short for "surface active agent," a surfactant consists of a hydrophilic moiety, which attracts water, and a hydrophobic moiety, which attracts oil and dirt. The amphiphilic structure of surfactant molecules enables them to suspend dirt, emulsify, and modify surface properties of materials. Variations in the chemical structure of a surfactant molecule can enable tunable properties, such as emulsifying capability (hydrophilic/lipophilic balance), oil/dirt suspension capacity (critical micelle concentration), cold water performance (Krafft point), foaming, and biodegradation.

Surfactants have generally been synthesized from petrochemical feedstocks, such as long chain alkanes/alkenes and ethylene oxide. However, surfactants synthesized from petrochemical feedstocks can present a number of issues. For one, such surfactants include chemicals that can be harmful to the environment. Moreover, such surfactants may not perform as intended in certain applications. For example, despite decades of development, these various surfactant structures are faced by a unified problem—the presence of hard water (e.g., containing calcium, magnesium, iron, etc.) inactivates these surfactants. When inactivation occurs, this causes surfactants to form solid precipitates and substantially lose the intended functionality.

To address these issues associated with surfactants synthesized from petrochemical feedstocks, surfactants are beginning to be derived from natural sources, including coconut oil, soybean oil, and sugars. The development has mainly focused on replacing the petrochemical surfactants with bio-based analogues having identical chemical structure (e.g., sodium lauryl sulfate from petroleum and sodium coco sulfate from coconut oil). The result is a surfactant that is more eco-friendly. To solve the problem of surfactant inactivation in the presence of hard water, a new class of bio-based surfactants, called oleo-furan surfactants ("OFS" or "OFSs") has been developed. In fact, OFSs have demonstrated 50-100 times greater calcium tolerance compared with other surfactants.

While OFSs can solve issues associated with surfactants synthesized from petrochemical feedstocks, the current method used for synthesizing OFSs has its own issues. The current method is a multi-step process with a purification phase included between each step in the process in order to separate out byproducts. The current method is inefficient, complex, difficult to scale and, moreover, can consume a relatively large amount of energy while at the same time producing a relatively large number of byproducts. In addition to being detrimental to the environment, this method can hamper the value of OFSs because it makes it more difficult for OFS to compete economically with petrochemical surfactants.

SUMMARY

In general, various exemplary embodiments relating to devices, systems, and methods for forming surfactants are disclosed herein. More particularly, various exemplary embodiments relating to devices, systems, and methods for forming furan based surfactants by reactive distillation are disclosed herein. For instance, such embodiments can provide a consolidated reaction process that uses reactive distillation to synthesize oleo-furan surfactant ("OFS" or "OFSs") molecules and intermediates by combining reaction and separation steps into a single reaction unit. Moreover, in this reactive distillation, catalyst materials, catalyst packing height/location, and/or distillation column operating conditions can be varied such that the combined reaction and distillation process can be tuned to achieve high yield and high purity of a desired OFS.

These embodiments may be useful, for instance, in facilitating a more simplistic and efficient method for synthesizing OFSs. As a result, this can allow OFS synthesis to be scaled thereby allowing OFSs to compete economically with petrochemical surfactants while still being more eco-friendly and preventing surfactant inactivation in the presence of hard water. In addition, as compared to the prior method for synthesizing OFSs, the present method can lessen the environmental impact due to reduced energy consumption and fewer resulting byproducts.

One exemplary embodiment includes a method of forming a surfactant. The method can include the step of introducing a triglyceride into a distillation column having a catalyst material contained at a catalyst bed within the distillation column. The method can also include the step of separating a first material from a second material within the distillation column, where the first material is separated to a first region within the distillation column that is above the catalyst bed and the second material is separated to a second region within the distillation column that is below the catalyst bed. The method can further include the step of removing the first material from the distillation column at a first outlet at the first region and removing the second materials from the distillation column at a second outlet at the second region. In addition, the method can include the step of forming an oleo-furan surfactant at a region within the distillation column that is below the catalyst bed.

The exemplary method embodiment can include the step of performing one or more of, including each of, the following reactions within a single distillation column or multiple, fluidly interconnected distillation columns (e.g., having features that are the same as, or similar to, those described for the distillation column immediately above): triglyceride hydrolysis to form a fatty acid and glycerol, anhydride synthesis of fatty acids into fatty acid anhydrides, and acylation of the fatty acid or fatty acid anhydride with furan to form an alkylfuran ketone. In a further embodiment, the exemplary method embodiment can include the step of performing one or both of the following reactions within that single distillation column or multiple, fluidly interconnected distillation columns: hydrogenation (or reduction) of alkylfuran ketone to alkylfuran or an alkylfuran alcohol, and alkoxylation (e.g. ethoxylation, propoxylation) of the alkylfuran to an alkoxylated form.

Another exemplary embodiment includes a distillation column device. The distillation column device includes a first catalyst bed, a first fluid medium space defined above the first catalyst bed, and a second fluid medium space defined below the first catalyst bed. In some embodiments, the distillation column device can further include an inlet of the distillation column at the first fluid medium space, a first outlet of the distillation column at the first fluid medium space, and a second outlet of the distillation column at the second fluid medium space such that one or more compositions output at the second outlet have passed through the first catalyst bed. In some cases, the fluid medium space may include one of inert packing material(s) and distillation tray(s). The first catalyst bed can be adapted to carry out a reaction with fluid received from the inlet.

In a further such embodiment, the distillation column device can additionally include a second catalyst bed, below the second fluid medium space, and a third fluid medium space defined below the second catalyst bed. In such an embodiment, the second outlet could be at the third fluid medium space, instead of the second fluid medium space, such that in this further embodiment one or more compositions output at the second outlet have passed through the first catalyst bed and the second catalyst bed. The second catalyst bed can include a different catalyst composition than that of the first catalyst bed and the first and second catalyst beds can be spaced apart from one another within the distillation column by the second fluid medium. In one example, the first catalyst bed and the second catalyst bed each respectively include a holding object secured to the distillation column where the holding object includes a catalyst material packed at the holding object.

In yet a further such embodiment, the distillation column device can additionally include a third catalyst bed, below the third fluid medium space, and a fourth fluid medium space defined below the third catalyst bed. In this further embodiment, the second outlet could be at the fourth fluid medium space, instead of the second or third fluid medium space, such that in this further embodiment one or more compositions output at the second outlet have passed through the first catalyst bed, the second catalyst bed, and the third catalyst bed. Each of the first catalyst bed, the second catalyst bed, and the third catalyst bed can include a different catalyst composition and the first, second, and third catalyst beds can be spaced apart from one another within the distillation column by the second and third fluid mediums, respectively.

A further exemplary embodiment includes a system of distillation column devices. The system can include a first distillation column device and a second distillation column device. The first distillation column device can be fluidly connected to the second distillation column device such that the system is configured to convey a fluid output from the first distillation column device to a fluid input of the second distillation column device. The first and second distillation column devices can be similar to any one of the exemplary distillation column device embodiments described above. For instance, the first distillation column device may have at least the first catalyst bed, the first fluid medium space, and the second fluid medium space while the second distillation column device may have at least the second catalyst bed and the third fluid medium space. In such an example, a composition that has passed through the first catalyst bed in the first distillation column device can be output, via the fluid connection therebetween, to the second distillation column device and pass through the second catalyst bed in the second distillation column device.

Another embodiment includes a method of forming a surfactant. This method embodiment includes providing a fatty acid at a second fluid medium space within a distillation column device. The distillation column device includes a first catalyst bed containing a first catalyst material within the distillation column. The second fluid medium space is above the first catalyst bed and a first fluid medium space is below the first catalyst bed within the distillation column device. This method embodiment also includes performing an acylation of the fatty acid with a furan-based structure at the first catalyst bed to form an alkylfuran ketone at the first fluid medium space within the distillation column device.

In one application of this method embodiment, the fatty acid provided at the second fluid medium space can be a fatty acid anhydride and performing the acylation then includes performing the acylation of the fatty acid anhydride with the furan-based structure at the first catalyst bed. In this application, providing the fatty acid anhydride at the second fluid medium space within the distillation column device can include i) providing the fatty acid at a third fluid medium space within the distillation column device, where the distillation column device includes a second catalyst bed containing a second catalyst material within the distillation column, this second catalyst material being different than the first catalyst material and the third fluid medium space being above the second catalyst bed and the second fluid medium space being below the second catalyst bed within the distillation column device, and ii) performing a dehydration of the fatty acid at the second catalyst bed to form the fatty acid anhydride at the second fluid medium space within the distillation column device.

In another application of this method embodiment where the fatty acid provided at the second fluid medium space is a fatty acid, performing the acylation of the fatty acid with the furan-based structure can include direct acylation of the fatty acid with the furan-based structure without performing a dehydration of the fatty acid.

As one example, in various embodiments disclosed herein, the fatty acid can be a fatty acid methyl ester, such as lauric acid methyl ester.

An additional embodiment includes a distillation column device. The distillation column device includes a first catalyst bed containing a first catalyst material within the distillation column device, a first fluid medium space below the first catalyst bed within the distillation column device, and a second fluid medium space above the first catalyst bed within the distillation column device. The first catalyst bed is configured to acylate a fatty acid anhydride with a furan-based structure to form an alkylfuran ketone at the first fluid medium space within the distillation column device.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following description. Embodiments of the invention will hereinafter be described in conjunction with the appended drawings, wherein like reference characters denote like elements.

DETAILED DESCRIPTION

Figure 1:
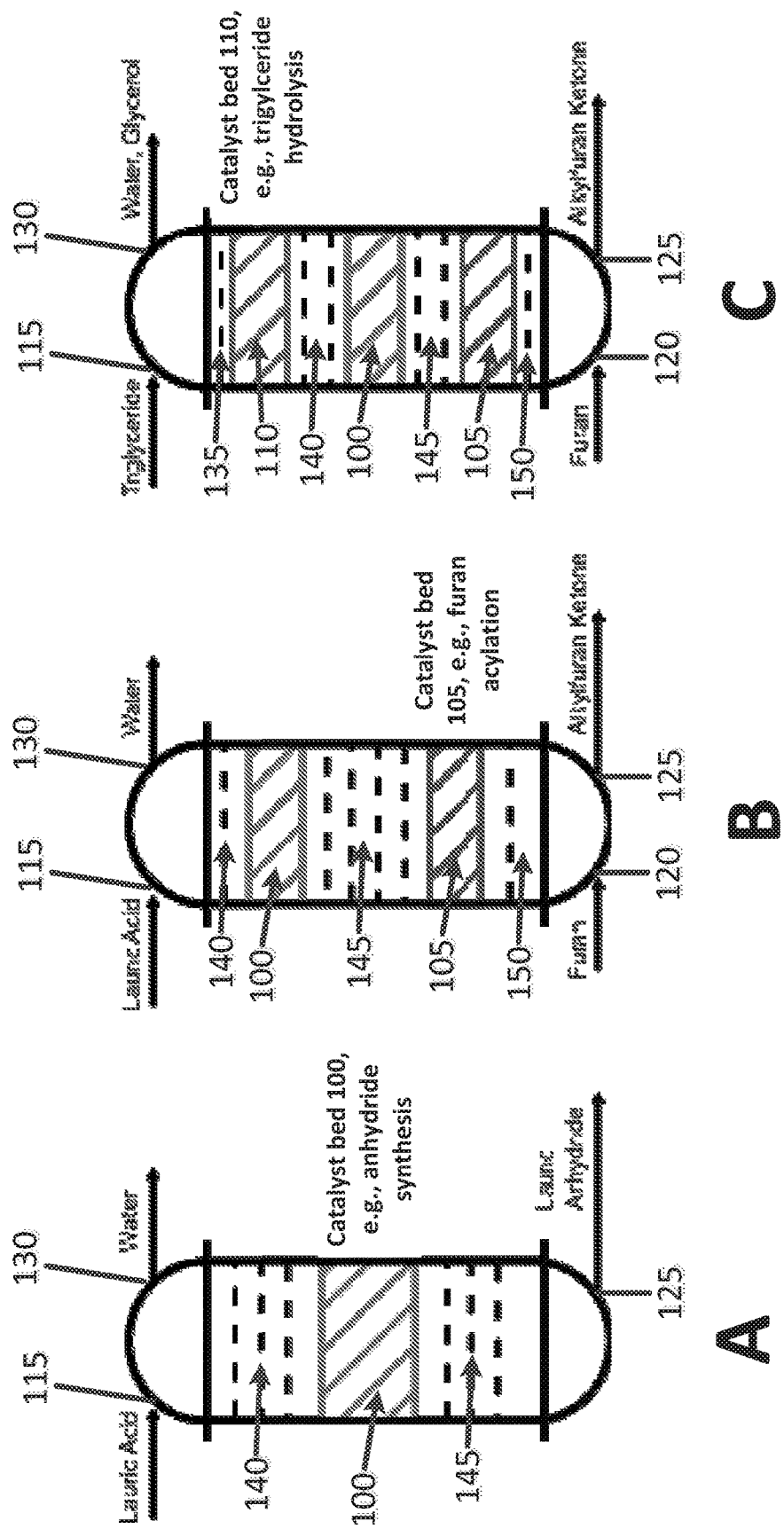
FIG. 1 is a schematic, elevational illustration of a number of distillation column device embodiments that can each be used to form a surfactant by reactive distillation.

The following detailed description is exemplary in nature and is not intended to limit the scope, applicability, or configuration of the invention in any way. Rather, the following description provides some practical illustrations for implementing exemplary embodiments of the present invention. Examples of constructions, materials, geometries, and/or dimensions are provided for selected elements. Those skilled in the art will recognize that many of the noted examples have a variety of suitable alternatives.

Examples of OFS structures and methods of synthesis are disclosed in international application publication numbers WO 2017/079718 and WO 2017/079719, the entire contents of each of which are hereby incorporated by reference. In these publications, OFSs are synthesized using a multi-step process. This multi-step process includes distinct process steps that include hydrolysis of a triglyceride molecule to form fatty acids, purification, dehydration of the fatty acids to form fatty acid anhydrides, purification, and acylation of furan with a fatty acid anhydride. Notably, between each step there is a purification phase to separate out byproducts, solvents, and products. Furthermore, subsequent steps in this process can include optional reactions, such as reduction/hydrogenation of oxygen functionality or aldol condensation to incorporate chemical branched structures, as well as chemical modification of the furan moiety with sulfonates, sulfates, or other oxygen moieties to form a hydrophilic group.

Embodiments of the present disclosure can use reactive distillation to synthesize OFS molecules and intermediates in a consolidated reaction process that combines reaction and separation steps. In this way, embodiments of the present disclosure can synthesize OFSs—of the same, or similar, structure as that of the above publications—in a more simplistic and efficient manner. As a result, embodiments of the present disclosure can allow OFS synthesis to be scaled and thereby allow OFSs to better compete economically with petrochemical surfactants as compared to the multi-step process of the above publications. In addition, as compared to the multi-step process of the above publication, embodiments of the present disclosure can lessen the environmental impact due to reduced energy consumption and fewer resulting byproducts.

Reactive distillation in embodiments of the present disclosure can replace inert distillation column packing, as used in conventional distillation, with active catalyst materials that are intended to carry out a chemical reaction. In various embodiments of the present disclosure, the use of the term "distillation column" is to be understood to include a trickle-bed reactor. The combined reaction and distillation process can be tuned in various embodiments to achieve relatively high yield and high purity of the particular desired OFS by varying the catalyst materials, catalyst packing height/location, and/or distillation column operating conditions. Exemplary reactive distillation steps, illustrated in Reaction Scheme 1 below, can include any one or more, including all, of (1) hydrolysis of a triglyceride (e.g., coconut oil), (2) dehydration of fatty acids to form fatty acid anhydrides (e.g., cocinic anhydride), (3) acylation of a fatty acid or fatty acid anhydride with a furan moiety to form alyklfuran ketones, (4) reduction/hydrogenation to remove oxygen and/or alkene functionalities, and (5) ethoxylation/propoxylation or other reactions to increase oxygen content of a portion of the molecule. Multiple reactions can be carried out in multiple catalytic zones in the same distillation column or in separate connected columns (e.g., connected in series). Exemplary Reaction Scheme 1 is show as follows, where reaction steps are combined to synthesize alkylfuran ketones from triglycerides and furan:

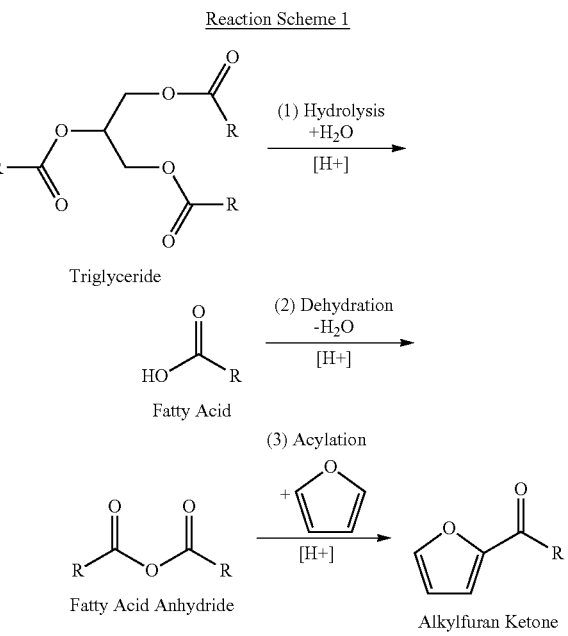

A feature in the development of this reactive distillation process according to various embodiments of the present disclosure is the management of reaction side products. For instance, since triglyceride hydrolysis consumes water and anhydride synthesis forms water, one such managed side product can be water. Managing reaction side products can be beneficial as the interaction of certain side products with reactants or catalysts can cause undesirable consequences, for instance, the interaction of water, or other side products (e.g., glycerol), with reactants or catalysts can cause side reactions and/or deactivation.

Various embodiments of the present disclosure can use reactive distillation to separate and help manage concentrations of reactants and products in catalytic zones. This can act to maximize product yields and minimize catalyst deactivation. In a reactive distillation column device, heavy products, such as alkylfurans or alkylfuran ketones, remain in liquid state and settle at or near the bottom the column. At the same time, in the reactive distillation column device light compounds, such as furan and water, volatilize and settle at or near the top of the column. As a result, in certain embodiments, the desired product (e.g., alkylfuran ketone) can be collected at the bottom of the column. In addition, in certain embodiments, a reflux condenser at the top of the column can be used to recycle a prescribed amount of volatile materials back to the column. Thus, embodiments of the present disclosure can efficiently use reactive distillation to maximize product yields and minimize undesirable deactivation.

Depending on the embodiment, a single distillation column or a number of distillation columns can be used to develop direct acylation of furan with carboxylic acids from triglycerides followed by hydrogenation and ethoxylation/propoxylation by reactive distillation. In those embodiments where two or more distillation columns are used, these distillation columns can be interconnected, either in series or in parallel, with liquid-liquid extraction separation in between the distillation columns. As one example, in such fluidly connected distillation column device embodiments, the number of distillation columns may range from two to seven. Though in other embodiments there can be other numbers of fluidly connected distillation column devices.

The particular configuration of the one or more distillation column devices can vary depending on a number of variables as a function of particular applications all within the scope of the present disclosure. These can include, for instance, the desired yield, process efficiency, and/or type of catalytic conversion of reactants to products. As illustrative examples of dimensions, distillation column height may vary from approximately two to two hundred feet and distillation column width (e.g., diameter) may vary from approximately a half inch to twenty feet. The one or more distillation columns can contain one or more distillation plates, packed column regions, or a mixture thereof, which can act to achieve desired catalytic conversion of reactants to products as well as efficient separation of products from other process components.

FIG. 1 provides a schematic, elevational illustration of distillation column device embodiments that can be used for reactive distillation. In particular, FIG. 1 illustrates an exemplary distillation column device A, an exemplary distillation column device B, and an exemplary distillation column device C. Within each distillation column is at least one catalyst bed 100. A reaction can occur on each of the one or more catalyst beds within the distillation column. Depending on the particular catalyst bed, in some embodiments two or more reactions can share a single catalyst bed. As shown in the illustrated examples, distillation column A includes one catalyst bed 100, distillation column B includes two catalyst beds 100, 105, and distillation column C includes three catalyst beds 100, 105, 110. Each catalyst bed 100, 105, 110 can contain a different catalyst material. Where two or more catalyst beds are included, as in distillation columns B (catalyst beds 100, 105) and C (catalyst beds 100, 105, 110), the order of the catalyst beds within the distillation column can vary depending on the operating conditions and recycle streams of that particular distillation column. Moreover, depending on the operating temperature of the particular catalyst bed, supplemental heaters may be required within the catalyst bed to reach temperatures sufficient for favorable conversion for each intended reaction. Recycle streams may be needed for components with low retention time within the distillation columns (e.g., furan, ethylene oxide, propylene oxide, and/or hydrogen) or for components with low conversion (e.g., fatty acid anhydrides, fatty acids, triglycerides, alkylfuran ketones, alkylfurans and/or water).

Each distillation column device A, B, and C can include a fluid inlet 115 adapted to receive one or more feedstocks into the distillation column. In some cases, two or more inlets can be included at a distillation column device for inputting one or more feedstocks, for instance two different types of feedstocks, into the distillation column device. For example, each of distillation column device B and distillation column device C includes the fluid inlet 115 and a second fluid inlet 120. In the illustrated embodiments, fluid inlets 115 and 120 are located at different elevations on the distillation column device B, C such that one or more catalyst beds 100, 105, 110 are located between the inlets 115, 120. The inlets 115, 120 can be used to input different materials into the distillation column device B, C at these different elevational locations on the distillation column device B, C. Feedstocks supplied into the distillation column can include, for instance, but are not limited to, fatty acids with chain lengths varying from (e.g., $C_3$ to $C_{26}$), for instance a fatty acid methyl ester (e.g., lauric acid methyl ester), triglycerides both mixed and homotriglycerides with chains lengths varying from ($C_3$ to $C_{26}$) these can be saturated or unsaturated (mono-, di-, or tri-), furan or furan derivatives, trifluoroacetic anhydride, acetic anhydride, and solvents.

As also shown in the illustrated embodiments, each distillation column device A, B, C can include a fluid outlet 125 adapted to output a synthesized material. In some cases, two or more outlets can be included at the distillation column device for outputting different materials. For example, the illustrated embodiments of the distillation column devices A, B, C include a second fluid outlet 130. In the illustrated embodiments, fluid outlets 125, 130 are located at different elevations on the distillation column device A, B, C such that one or more catalyst beds 100, 105, 110 are located between the outlets 125, 130. For example, for the distillation column device C, the outlet 125 is located below each of the catalyst beds 100, 105 and 110 while the outlet 130 is located above each of the catalyst beds 100, 105, 110. The outlets 125, 130 can be used to output different materials from the distillation column device A, B, C at these different elevational locations on the distillation column device A, B, C. For example, the outlet 130 can be used to manage reaction side products. For instance, one or more side products, such as water and/or glycerol, can be output at the outlet 130 to enable the distillation column device A, B, C to reduce detrimental impact of such side products.

In addition, each distillation column device A, B, and C can include a solvent used for the reactive distillation and/or, when included as part of the particular method, subsequent liquid-liquid extractions. These solvents can include, for example, ketones including acetone and methylethylketone, hydrocarbons including, but not limited to, pentane, hexane, and heptane, cyclohexane, and cyclopentane, aromatic organics including benzene, toluene, organic nitriles including acetonitrile, propionitrile, and butyronitrile, organic chlorocarbons including dichloromethane, dichloroethane, chloroform, alcohols including, but not limited to, methanol, ethanol, and isopropanol, ethereal solvents including, but not limited to, dimethyl ether, diethyl ether, and tetrahydrofuran, esters including, but not limited to, methyl acetate and ethyl acetate, and water. Though, in certain embodiments, the distillation column could be absent of any solvent (sometimes referred to as "neat"). In some cases, it can be useful if the solvent used includes, but is not limited to, acetone, heptane, cyclohexane, toluene, xylene, acetontrile, methanol, ethanol, isopropanol, 1-butanol, ethyl acetate and isopropyl acetate, cyclopentyl methyl ether, 2-methyltetrahydrofuran, tetrahydrofuran, and water.

As noted, in one example a single distillation column or a number of interconnected distillation columns can be used to facilitate reactive distillation for developing direct acylation of furan with carboxylic acids from triglycerides followed by hydrogenation and ethoxylation/propoxylation. In this example, up to five reactions can occur on up to five different catalyst beds within the distillation column(s). For instance, where multiple distillation columns are used one to four reactions could occur within a first distillation column while the remainder of the five total reactions could occur within a second distillation column.

The present disclosure encompasses various combinations of reactions, including various combinations of the five reactions described as follows. Reaction one can be a triglyceride hydrolysis to form a fatty acid and glycerol. Reaction two can be an anhydride synthesis of fatty acids into fatty acid anhydrides. Reaction three can be an acylation of the fatty acid with furan to form an alkylfuran ketone. Reaction four can be a hydrogenation/reduction of alkylfuran ketone to alkylfuran or an alkylfuran alcohol. Reaction four may have operating conditions that are suitable for a continuous flow reactor over a fixed catalyst bed. Reaction five can be an alkoxylation (e.g. ethoxylation, propoxylation) of the alkylfuran to an alkoxylated form. In one method embodiment, two or more of any of reactions one, two, three, four, and five can be included. For instance, in a particular method embodiment each of reactions one, two, three, four, and five can be included. In another specific method embodiment, each of reactions two, three, four, and five can be included. Or, in another instance of a specific method embodiment, each of reactions two, three, and four can be included. As another illustrative example, in an additional method embodiment, each of reactions two, three, and five can be included. In a number of given method embodiments within the scope of this disclosure, the two or more of any of reactions one, two, three, four, and five that can be included may vary and be selected according to the specific application of the embodiment.

Table 1 is presented below and includes possible catalyst classes and types that can be used for one or more of (e.g., all of) reactions one through five described in the example above. All of the up to five catalyst beds of the one or more distillation columns may include a catalyst from Table 1. Catalyst beds in the one or more distillation column devices can include a single homogenous catalyst, a mixture of two or more catalysts with varying concentrations of the two or more catalysts, or a gradient of a catalyst where the catalyst slowly transitions from one catalyst to another different catalyst within a single catalyst bed. In some instances, it may be suitable for reactions one, two and three to occur on a highly acidic catalyst bed from Table 1. In addition, in some instances it may be suitable for reaction four to occur on a metal oxide catalyst bed from Table 1.

TABLE 1

| Family | Genus | Species | Example |
|---|---|---|---|
| Acid | Lewis Acid (L-Acid) Catalysts | L-Acid | $AlCl_3$, $TiCl_4$, $FeCl_3$, $BF_3$, $SnCl_4$, $ZnCl_2$, $ZnBr_2$, Amberlyst-15 |
| | | Supported L-Acid L-Acid/S | $SiO_2$, $Al_2O_3$, $ZrO_2$, $TiO_2$, $SiO_2$—$Al_2O_3$ |
| | BrØnsted Acid (B-Acid) Catalysts | B-Acid | HCl, HBr, HI, $HClO_4$, $HClO_3$, $HNO_3$, $H_2SO_4$, $CH_3COOH$, $CF_3COOH$, $H_3PO_4$ |
| | Solid Acid Catalysts | Zeolites, (Z) | H-ZSM-5, H-BEA, H-Y, Mordenite, Ferrierite |
| | | Substituted-Zeolites (Sub.) | Sn, Ge, Ti, Fe, Zr |
| | | Heteropolyacids (HPAs) | $H_3PW_{12}O_{40}$, $H_3SiW_{12}O_{40}$, $H_3PMo_{12}O_{40}$, $H_3SiMo_{12}O_{40}$ ($Cs^+$ substituted HPAs) |
| | | Phosphate ($PO4^{3-}$) | Niobium phosphate ($NbOPO_4$), Zirconium phosphate ($ZrO_2$—$PO_4$), Siliconiobium phosphate (Nb—P—Si—O) |
| | | Zirconia ($ZrO_2$) | $SO_3$—$ZrO_2$, $SiO_2$—$ZrO_2$, Zeolites-$ZrO_2$, $Al_2O_3$—$ZrO_2$, $WO_x$—$ZrO2$ |
| | | Carbon (C) | Sulfated carbon ($SO_3$H-functionalized carbon) |
| Base | Solid Base Catalysts | Supported Alkalais | $KF/Al_2O_3$, $K_2CO_3/Al_2O_3$, $KNH_2/Al_2O_3$, $NaOH/Al_2O_3$, $KOH/Al_2O_3$ |
| | | Zeolites, Clays | K, Rb, Cs-exchanged X-zeolites, ETS-10, Sepiolite, |
| | | Phosphates | Hydroxyapatite, natural phosphates |
| | | Amides, imines, amines, or ammonium ions on support | KNH2/Al2O3, K, Y, Eu supported on zeolites |
| | | Metal Oxide, Mixed Metal Oxide | MgO, CaO, Mg—Zr—O, Mg—Si—O, Mg—Al—O |
| | Homogeneous Base | Organic & Inorganic | pyridine, imidazole, ammonia |
| Metal | Metallic | Precious metals, alkalai or alkaline earth metals | Pt, Pd, Ni, Cu, Al, Zn, Au, Ag, Sn |
| | Bimetallic | Transition-Transition or Precious-Transition metals | Pd—Cu, Cu—Ni, Cu—Cr, Ni—Pt, Ni—Pd, Ni—Sn |
| | Metal Oxide | Metal oxides, Rare earth oxides, Alkali metal oxides | NiO, $ZnO_2$, CuO, Cu—Cr—O, Cu—Ni—O, Cu—Al—O, $Al_2O_3$, $ZrO_2$, $La_2O_3$ |

For example, the catalyst material(s) contained at the catalyst bed 100, the catalyst material(s) contained at the catalyst bed 105, and the catalyst material(s) contained at the catalyst bed 110 can be selected from any one or more listed in Table 1. While the catalyst classes and types shown in Table 1 can be used at the catalyst beds 100, 105, 110 for one or more of (e.g., all of) reactions one through five described in the examples herein, certain catalysts may be preferably in certain applications. For example, the catalyst material(s) contained at the catalyst bed 100, the catalyst material(s) contained at the catalyst bed 105, and the catalyst material(s)

contained at the catalyst bed 110 can be selected from the following: H-Bea, HY, Ultrastable-Y, MCM-41, SBA-15, tungstated zirconia, sulfated zirconia, amorphous silica, Nafion NR-50, Nafion SAC-13, or Nafion deposited on a support such as silica.

As shown in FIG. 1, the catalyst bed is contained to a particular region within the distillation column. For instance, the catalyst bed can be contained within the distillation column at a region that is bounded above and below by a fluid medium space. Or, in embodiments where two or more catalyst beds are included, each of the catalyst beds can be contained to its own particular region within the distillation column with a fluid medium space defined within the distillation column between each catalyst bed as well as above the uppermost catalyst bed and below the lowermost catalyst bed. The catalyst bed(s) can be contained to the respective particular region within the distillation column by packing the one or more catalysts onto an object, such as cloth or wire mesh, which is secured within the distillation column. For example, the one or more catalysts can be compressed into a particulate, such as pellets. When used, the cloth can be made of, for example, synthetic or organic materials, such as polyester, cotton, or Teflon. When used, the mesh material for packing the catalyst can include stainless steel or aluminum.

For example, in one particular application, the exemplary embodiment of the distillation column device C as illustrated in FIG. 1 can carry out a number of the described reactions for synthesizing an alkylfuran ketone. For instance, at the inlet 115 a triglyceride can be introduced into a fluid medium space 135 that is within the distillation column device C above the catalyst bed 110. At the catalyst bed 110, a first reaction, triglyceride hydrolysis, can take place to from one or more fatty acids and glycerol. The resulting glycerol, and water, can be a side product that is removed at the outlet 130. The resulting one or more fatty acids can then be provided at a fluid medium space 140 that is within the distillation column C and between the catalyst bed 110 (e.g., fluid medium space 140 is below the catalyst bed 110) and the catalyst bed 100 (e.g., fluid medium space 140 is above the catalyst bed 100). At the catalyst bed 100, a second reaction, an anhydride synthesis of the one or more fatty acids, can take place to form one or more fatty acid anhydrides. The resulting one or more fatty acid anhydrides can then be provided at a fluid medium space 145 that is within the distillation column C and between the catalyst bed 100 (e.g., fluid medium space 145 is below the catalyst bed 100) and the catalyst bed 105 (e.g., fluid medium space 145 is above the catalyst bed 105). At the catalyst bed 105, a third reaction, an acylation of the fatty acid with a furan-based structure (e.g., from the inlet 120), can take place to form an alkylfuran ketone. The resulting alkylfuran ketone can be output at the outlet 125.

This third reaction, acylation of the fatty acid with a furan-based structure, could be performed using a number of various furan-based structures. For example, the furan-based structure used for the acylation of the fatty acid can be one of the following furan-based structures:

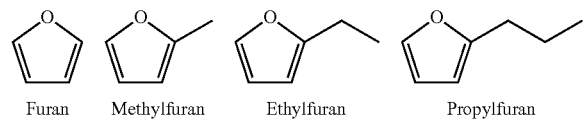

Furan   Methylfuran   Ethylfuran   Propylfuran

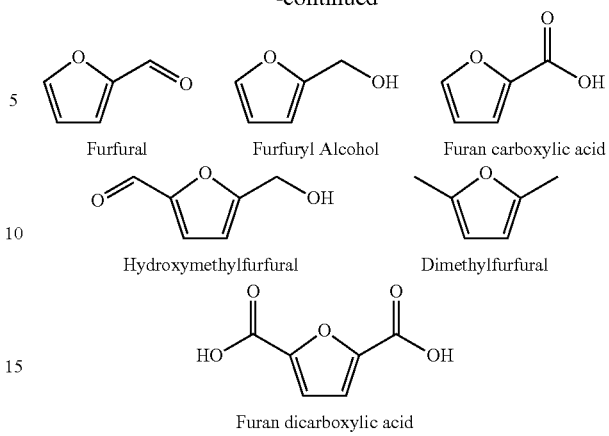

Furfural   Furfuryl Alcohol   Furan carboxylic acid

Hydroxymethylfurfural   Dimethylfurfural

Furan dicarboxylic acid

In a specific exemplary application, it may be preferable for the furan-based structure used for the acylation of the fatty acid to be selected from the group consisting of: furan and methylfuran.

In a further exemplary embodiment, additional reactions can be included involving the alkylfuran ketone, for instance also within the distillation column device C or within another, fluidly connected distillation column device. For example, a fourth reaction, a hydrogenation, or reduction, of the alkylfuran ketone, to form alkylfuran or an alkylfuran alcohol. In some cases, this fourth reaction may have operating conditions that are suitable for a continuous flow reactor over a fixed catalyst bed. Additionally, in some further examples, a fifth reaction, an alkoxylation (e.g. ethoxylation, propoxylation) of the alkylfuran, can take place to form an alkoxylated form. This can take place within the same distillation column as the fourth reaction or can take place in another, fluidly connected distillation column.

As shown in the embodiment of the distillation column device C, the catalyst beds 100, 105, 110 separate the fluid medium spaces 135, 140, 145, 150. In this way, materials are directed to distill at a respective fluid medium space and react at the respective catalyst bed before passing to the next fluid medium space for distillation and subsequent reaction at the next catalyst bed.

The exemplary embodiments of the distillation column device A, B are illustrated with like numerals as described with respect to the exemplary embodiments of the distillation column device C. As such, the exemplary embodiments of the distillation column device A, B can include the illustrated features for each and function in a manner similar as that described with respect to those corresponding features in the exemplary embodiments of the distillation column device C.

In some embodiments, inert packing materials or distillation trays can be used at one or more of the fluid medium spaces within the distillation column where no catalyst bed is present in order to improve separation efficiency. To facilitate proper separation of the products and byproducts, particular tray size or packing material within the distillation column can vary as suitable for the specific embodiment. Distillation column packing can be, for instance, randomly packed, grid packed, or structured packed. Trays used within the distillation column can be, for instance, bubble cap, sieve deck, dual flow, valve, or baffle trays.

In some embodiments, the reactions occurring within the distillation column may require relatively high pressures to keep compounds in liquid phases. In such embodiments, the distillation column could be operated under pressures ranging from 761 to 18,750 mmHg (2.5 MPa). This higher pressure can be created within the distillation column in a number of ways. As one example, the higher pressure can be supplied by an increase in temperature and/or introduction of gaseous hydrogen, helium, argon, nitrogen, air, ethylene oxide, propylene oxide, or steam. Such temperatures may range from 1-700° C. Moreover, in certain embodiments, vacuum distillation may be used to remove low volatility compounds. For example, vacuum distillation can operate with pressures ranging from approximately 0.001 mmHg to 759 mmHg.

Coking onto a catalyst bed may result in deactivation, which could detrimentally impact the functionality of the catalyst bed in the disclosed exemplary processes. To help prevent or remove any coking, oxidative regeneration can be implemented within the one or more distillation columns at a relatively high temperature ranging from approximately 100-800° C. under oxidative conditions. For instance, pure oxygen or a mixture of oxygen and a noble gas (e.g., helium, argon, neon) where oxygen has a concentration from 5-99% can be useful in removing the coke at the catalyst bed. Solid acid/base catalyst material can retain relatively large volumes of water. In some cases, during oxidative regeneration calcination of the catalyst bed may be needed with temperatures ranging from 100-800° C. under static air, forced dry air, nitrogen, or other gases.

Figure 2:
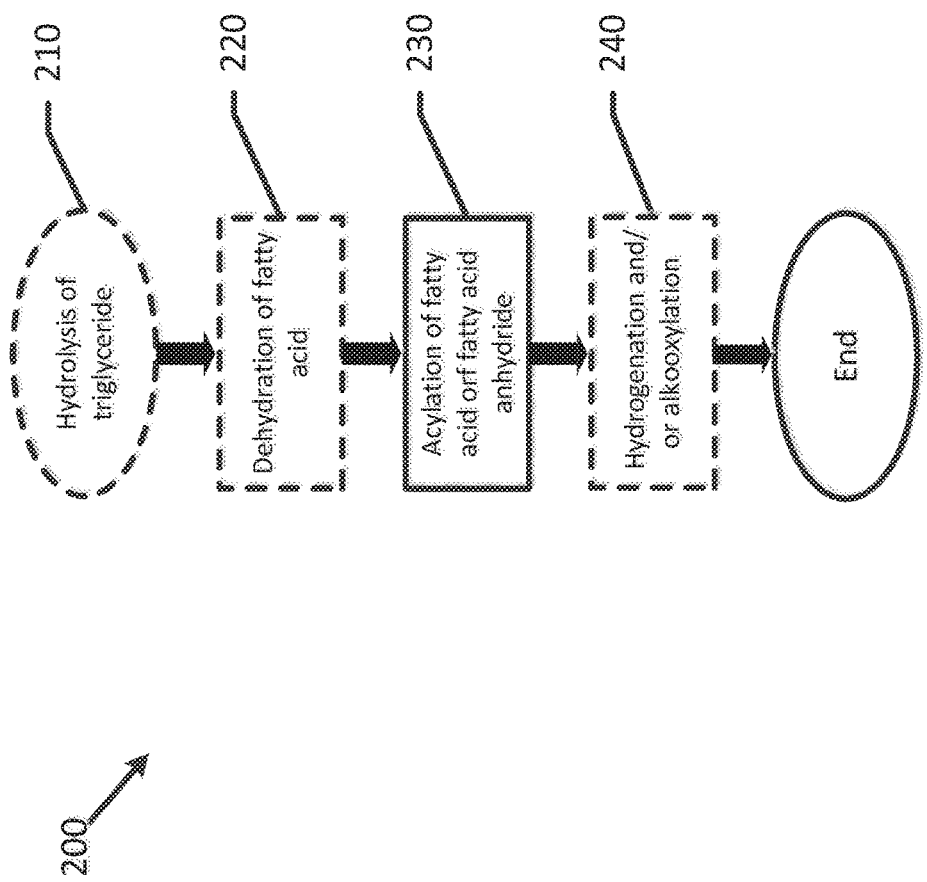
FIG. 2 is a flow diagram of an embodiment of a method of forming a surfactant by reactive distillation.

FIG. 2 shows a flow diagram of an embodiment of a method 200 of forming a surfactant by reactive distillation. For example, the method 200 could be carried out in one of the distillation column devices A, B, C disclosed previously herein. As another example, the method 200 could be carried out according to Reaction Scheme 1 disclosed previously herein.

At step 210, hydrolysis of a triglyceride takes place. For example, this hydrolysis at step 210 can take place at a catalyst bed within a distillation column device. For example, in some cases the triglyceride may be coconut oil. In some embodiments, step 210 may also include removing a side product, resulting from the hydrolysis, from the distillation column, such as glycerol and/or water.

At step 220, dehydration of one or more fatty acids takes place to form one or more fatty acid anhydrides, such as cocinic anhydride. For example, this dehydration at step 220 can take place at a catalyst bed within a distillation column device. The catalyst bed at which the dehydration of step 220 takes place can be below, and spaced apart from by a fluid medium space, the catalyst bed at which the hydrolysis at step 210 can take place.

At step 230, acylation of a fatty acid, or a fatty acid anhydride, with a furan-based structure takes place to form one or more alkylfuran ketones. For example, this acylation at step 230 can take place at a catalyst bed within a distillation column device. The catalyst bed at which the acylation of step 230 takes place can be below, and spaced apart from by a fluid medium space, the catalyst bed at which the dehydration at step 220 can take place. The furan-based structure used in step 230 can be, for instance, furan or methylfuran. For instance, if a fatty acid is acylated at step 230, the fatty acid could be a fatty acid methyl ester.

At step 240, one or both of i) reduction (or hydrogenation) to remove oxygen functionality and ii) ethoxylation (or propoxylation) or other reactions to increase oxygen content of a portion of the molecule can take place. The removal or increase of oxygen at step 240 may take place within the same distillation column device as the other steps of the method 200 or can take place in a separate, but fluidly connected, distillation column device.

In one embodiment of a method of forming a surfactant by reactive distillation, some of the steps shown in FIG. 2 need not necessarily be performed. For example, one method of forming a surfactant by reactive distillation can include only step 230 and one or more of the other steps described with respect to FIG. 2 (e.g., steps 210, 220, and/or step 240) need not take place by reactive distillation.

While exemplary features of the distillation column(s) and related methods have been described, the following will describe additional details as to these methods facilitated by the described distillation column(s). The single distillation column or number of interconnected distillation columns can be used in a process for a high-throughput, tandem process for preparing biodegradable surfactants from fatty acids and furan. This can involve reaction steps that combine triglyceride hydrolysis, fatty acid anhydride production via dehydration of the resulting fatty acid, and acylation of the anhydride with furan sourced from sugar to produce alkylfuran ketone surfactant precursors. Additional reactions can include reduction/hydrogenation steps, as well as alkoxylation. The following provides some specific examples to further illustrating the high-throughput, tandem process that can be facilitated through use of the distillation column(s). Though, it is to be understood that a variety of other alternatives could be suitable depending on the particular application.

As to hydrolysis of triglycerides, palm oil triglycerides can be combined with a macroporous resin (e.g., CT-165 resin) and heated to a temperature in the range of approximately 120-155° C. over a time period of approximately 0.25-14 hours. In some instances, a constant injection of steam can be used during the reaction. In many such reactions, five grams of catalyst per 100 mL of triglyceride can be combined in a round bottom flask and immersed in a constant temperature bath. The mixture can then be agitated with a mechanical stirrer and also constantly supplied steam with a steam injector. Upon complete conversion to the fatty acid, catalyst can be removed by filtration and residual water can be removed by heated vacuum.

As to fatty acid anhydride production, in one exemplary case a carboxylic acid can reacted with a dehydrating agent, including, but not limited to, acetic anhydride and propionic anhydride, in liquid phase in the presence of an azeotroping agent, including toluene, ethyl benzene, or tetrachloroethylene. The combination can be heated in the temperature range of 100-160° C. to achieve a continuous boil. Pressure can then be reduced to remove the corresponding acid of the dehydrating agent, water, and azeotroping agent. In some such reactions, 1-part carboxylic acid is combined with 37-parts of the azeotroping agent and 6-parts dehydrating agent in a round bottom flask equipped with a fractionating column. The reaction mixture can be heated until arriving at 150° C., at which point the pressure is decreased until only the product remained in the reaction flask.

Again as to fatty acid anhydride production, in another exemplary case a fatty acid ($C_3$-$C_{26}$) can be reacted with a dehydrating agent, including, but not limited to, acetic anhydride and propionic anhydride, in liquid phase in a temperature range of approximately 25-150° C. over a time period ranging from approximately 5-30 minutes. This process may be carried out in the absence of solvent or catalyst in certain instances. Further purification of the anhydride product to remove asymmetric anhydride impurities can be achieved by continuous removal of the dehydrating agent under reduced pressure in the range of approximately 500 to 1 mm Hg while sustaining a temperature in the range of approximately 100-160° C. over a time period ranging from approximately 0.1-60 minutes. Complete purification of the symmetric anhydride product can be achieved, in some instance, by thin-film short path evaporation under reduced pressure in the range of approximately 1 to 0.001 mm Hg while sustaining a temperature in the range of approximately 100-220° C. over a time period ranging from approximately 0.01-1 minute. In certain such reactions, equimolar amounts of the fatty acid and dehydrating agent can be combined in a round bottom flask under inert atmosphere with magnetic stirring. The flask may be fitted with a Vigreux distillate column and a distillate condenser, and the reaction can be heated under partial vacuum until full conversion to the symmetric anhydride product is achieved. At this time, full vacuum can be applied to remove the corresponding acid of the unreacted dehydrating agent corresponding acid. Short path evaporation can then be used to remove the remaining fatty acid starting material and asymmetric anhydrides to complete purification.

Further as to fatty acid anhydride production, in yet another exemplary case a relatively higher carboxylic acid ($C_1$-$C_{20}$) can be reacted in a temperature range of 140-220° C. in liquid phase in the presence of certain metal salts, including, but not limited to, metal acetate hydrate salts, $M^x(OAc)_x \cdot YH_2O$, where the metal is Co, Mn, Fe, Cr, Cu, and Pd, over a time period in the range of approximately 1-5 hours. This process can be carried out in hydrocarbon solvents including, but not limited to, heptane, benzene, and toluene. It can be useful to carry this out in an inert atmosphere. In many such reactions, a glass reactor fitted with a mechanical stirrer can be charged with the carboxylic acid and a ten-fold molar excess of the metal acetate salt in addition to a small volume of solvent, then fitted with, for instance, a Dean stark trap filled with solvent. Over approximately three hours of stirring vigorously at approximately 200° C., the removed water can be collected in the Dean Stark tube, the metal salt can be removed by filtration, and the anhydride product can be further isolated from the solvent and starting material by rotary evaporation.

As to acylation of furan with fatty acid anhydrides, a variety of processes can be included as part of the method encompassed by embodiments of the present disclosure. As one example, any one or more of those processes disclosed in WO 2017/079718 and WO 2017/079719, and previously incorporated herein, can be used.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A method of forming a surfactant, the method comprising:
    providing a fatty acid at a second fluid medium space within a distillation column device, the distillation column device including a first catalyst bed containing a first catalyst material within the distillation column, the second fluid medium space being above the first catalyst bed and a first fluid medium space being below the first catalyst bed within the distillation column device; and
    performing an acylation of the fatty acid with a furan-based structure at the first catalyst bed to form an alkylfuran ketone at the first fluid medium space within the distillation column device.

2. The method of claim 1, wherein the furan-based structure is selected from the group consisting of: furan and methylfuran.

3. The method of claim 1, wherein the first catalyst material is selected from the group consisting of: H-Bea, HY, Ultrastable-Y, MCM-41, SBA-15, tungstated zirconia, sulfated zirconia, and amorphous silica.

4. The method of claim 1, wherein the fatty acid provided at the second fluid medium space is a fatty acid anhydride, and wherein performing the acylation comprises performing the acylation of the fatty acid anhydride with the furan-based structure at the first catalyst bed.

5. The method of claim 4, wherein providing the fatty acid anhydride at the second fluid medium space within the distillation column device comprises:
    providing the fatty acid at a third fluid medium space within the distillation column device, the distillation column device including a second catalyst bed containing a second catalyst material within the distillation column, the second catalyst material being different than the first catalyst material, the third fluid medium space being above the second catalyst bed and the second fluid medium space being below the second catalyst bed within the distillation column device; and
    performing a dehydration of the fatty acid at the second catalyst bed to form the fatty acid anhydride at the second fluid medium space within the distillation column device.

6. The method of claim 5, wherein providing the fatty acid at the third fluid medium space within the distillation column device comprises:
    providing a triglyceride at a fourth fluid medium space within the distillation column device, the distillation column device including a third catalyst bed containing a third catalyst material within the distillation column, the third catalyst material being different than the first catalyst material and the second catalyst material, the fourth fluid medium space being above the third catalyst bed and the third fluid medium space being below the third catalyst bed within the distillation column device; and
    performing a hydrolysis of the triglyceride at the third catalyst bed to form the fatty acid at the third fluid medium space within the distillation column device.

7. The method of claim 6, wherein providing the triglyceride comprises inputting the triglyceride into the distillation column device at a first fluid inlet of the distillation column device, the first fluid inlet being at a first elevation on the distillation column device that is above the third catalyst bed.

8. The method of claim 6, further comprising:
    outputting, from the distillation column device, at a first fluid outlet on the distillation column device a side product generated by hydrolysis of the triglyceride, the first fluid outlet being at a first elevation on the distillation column device that is above the third catalyst bed.

9. The method of claim 8, further comprising:
    outputting, from the distillation column device, at a second fluid outlet on the distillation column device the alkylfuran ketone, the second fluid outlet being at a second elevation on the distillation column device that is below the first catalyst bed.

10. The method of claim 1, wherein the fatty acid provided at the second fluid medium space is a fatty acid anhydride, and wherein the first fluid medium space and the second fluid medium space are separated by the first catalyst bed such that the fatty acid anhydride passing from the second fluid medium space to the first fluid medium space must pass through the first catalyst bed.

11. The method of claim 1, further comprising:
hydrogenation of the alkylfuran ketone to alkylfuran.

12. The method of claim 11, wherein the hydrogenation is performed within the distillation column device.

13. The method of claim 11, wherein the alkylfuran ketone passes from the distillation column device to a second distillation column device that is fluidly connected to the distillation column device, and wherein the hydrogenation is performed within the second distillation column device.

14. The method of claim 11, further comprising:
alkoxylation of the alkylfuran to an alkoxylated form.

15. The method of claim 14, wherein the hydrogenation and the alkoxylation are performed within the distillation column device.

16. The method of claim 1, wherein performing the acylation of the fatty acid with the furan-based structure comprises direct acylation of the fatty acid with the furan-based structure without performing a dehydration of the fatty acid.

17. The method of claim 1, wherein the fatty acid is a fatty acid methyl ester.

18. A distillation column device comprising:
a first catalyst bed containing a first catalyst material within the distillation column device;
a first fluid medium space below the first catalyst bed within the distillation column device; and
a second fluid medium space above the first catalyst bed within the distillation column device,
wherein the first catalyst bed is configured to acylate a fatty acid with a furan-based structure to form an alkylfuran ketone at the first fluid medium space within the distillation column device.

19. The device of claim 18, wherein the fatty acid is a fatty acid anhydride, and further comprising:
a second catalyst bed containing a second catalyst material within the distillation column device, the second catalyst material being different than the first catalyst material; and
a third fluid medium space above the second catalyst bed, the second fluid medium space below the second catalyst bed,
wherein the second catalyst bed is configured to dehydrate the fatty acid to form the fatty acid anhydride at the second fluid medium space within the distillation column device.

20. The device of claim 19, further comprising:
a third catalyst bed containing a third catalyst material within the distillation column device, the third catalyst material being different than the first catalyst material and the second catalyst material;
a fourth fluid medium space above the third catalyst bed, the third fluid medium space below the third catalyst bed, wherein the third catalyst bed is configured to hydrolyze a triglyceride to form the fatty acid at the third fluid medium space within the distillation column device;
a first fluid inlet to the fourth fluid medium space of the distillation column device, the first fluid inlet being at an elevation on the distillation column device that is above the third catalyst bed;
a first fluid outlet from the fourth fluid medium space of the distillation column device, the first fluid outlet being at an elevation on the distillation column device that is above the third catalyst bed; and
a second fluid outlet from the first fluid medium space of the distillation column device, the second fluid outlet being at an elevation on the distillation column device that is below the first catalyst bed.

* * * * *